United States Patent [19]
Niebylski

[11] Patent Number: 5,201,947
[45] Date of Patent: Apr. 13, 1993

[54] PRECERAMIC COMPOSITIONS AND CERAMIC PRODUCTS

[75] Inventor: Leonard M. Niebylski, Birmingham, Mich.

[73] Assignee: Ethyl Corporation, Richmond, Va.

[21] Appl. No.: 414,464

[22] Filed: Sep. 29, 1989

[51] Int. Cl.$^5$ .............................................. C09K 15/02
[52] U.S. Cl. ......................... 106/287.11; 106/287.19; 106/287.23; 528/8; 528/13; 556/402; 556/403
[58] Field of Search ................ 556/403, 402; 428/447; 501/96, 97, 88; 106/287.11, 287.19, 287.23; 528/8, 13

[56] References Cited

U.S. PATENT DOCUMENTS

| | | | |
|---|---|---|---|
| 2,957,900 | 10/1960 | Groszos | 556/403 |
| 3,029,210 | 3/1962 | Groszos | 556/403 |
| 4,493,855 | 1/1985 | Sachden et al. | 427/41 |
| 4,581,468 | 3/1986 | Paciorek et al. | 501/96 |
| 4,664,367 | 8/1986 | Takamizawa et al. | 501/95 |
| 4,762,810 | 8/1988 | Endo et al. | 501/88 |
| 4,873,353 | 10/1989 | Niebylski | 556/406 |
| 4,910,173 | 3/1990 | Niebylski | 528/4 |

Primary Examiner—Mark L. Bell
Assistant Examiner—David M. Brunsman
Attorney, Agent, or Firm—Patricia J. Hogan

[57] ABSTRACT

Preceramic compositions which have particular utility in providing protective ceramic coatings on carbon-/carbon composites, graphite, carbon fibers, and other normally oxidizable materials are prepared by dispersing about 0.4–1 part by weight of a metal boride in an organic solvent solution containing one part by weight of an organoborosilazane polymer prepared by mixing about 0.25–20 parts by weight of a trialkoxy-, triaryloxy-, or tri(arylalkoxy)boroxine with a solution of one part by weight of a polysilazane in an organic solvent.

8 Claims, No Drawings

PRECERAMIC COMPOSITIONS AND CERAMIC PRODUCTS

FIELD OF INVENTION

This invention relates to ceramic materials derived from polysilazanes and more particularly to such materials which are useful in protecting substrates that are normally susceptible to oxidative deterioration.

BACKGROUND

It is known that many materials, such as carbon/carbon composites, carbon fibers, graphite, and certain metals have properties which make them attractive for use in aerospace and other applications in which their susceptibility to oxidative deterioration at elevated temperatures is a serious disadvantage. It would be desirable to find a means of protecting those materials from oxidation at high temperatures, and it has been proposed to provide such protection with ceramic coatings. However, known ceramic coatings have proved to be inadequate.

As disclosed in U.S. Pat. Nos. 4,397,828 (Seyferth et al.-I) 4,482,669 (Seyferth et al.-II), 4,645,807 (Seyferth et al.-III), 4,650,837 (Seyferth et al.-IV), and 4,659,850 (Arai et al.), it is known that ceramics can be obtained from polysilazanes. U.S. Pat. No. 4,482,689 (Haluska) discloses boron-containing metallosilazane polymers which are also useful in forming ceramic materials.

SUMMARY OF INVENTION

An object of this invention is to provide novel organoborosilazane polymer compositions.

Another object is to provide such compositions which can be converted to ceramic coatings capable of protecting oxidizable substrates from oxidative deterioration at elevated temperatures.

A further object is to provide ceramic compositions having high thermal stability.

These and other objects are attained by intimately dispersing about 0.4-1 part by weight of a metal boride in an organic solvent solution containing one part by weight of an organoborosilazane polymer, said polymer having been prepared by mixing about 0.25-20 parts by weight of a trialkoxy-, triaryloxy-, or tri(arylalkoxy)-boroxine with a solution of one part by weight of a polysilazane in an organic solvent.

DETAILED DESCRIPTION

The organoborosilazane polymers employed in the practice of the invention are disclosed in copending applications Ser. No. 242,493 (Niebylski-I), filed Sep. 9, 1988, and Ser. No. 272,481 (Niebylski-II), filed Nov. 17, 1988, now U.S. Pat. No. 4,921,905.

As taught in the copending applications, the polysilazane which is reacted with the boroxine may be any polysilazane that is soluble in common organic solvents, such as aliphatic or aromatic hydrocarbons, dialkyl or alicyclic ethers, etc.; and it may be, e.g., a polysilazane of Seyferth et al.-I, Seyferth et al.-II, Seyferth et al.-III, Seyferth et al.-IV, or Arai et al., the teachings of all of which are incorporated herein in toto by reference. However, it is preferably a polysilazane of the type taught by Seyferth et al.-II, i.e., a polysilazane prepared by reacting an organodihalosilane with ammonia, treating the ammonolysis product with a basic catalyst which is capable of deprotonating an NH group that is adjacent to an SiH group, and quenching the resultant product with an electrophilic quenching reagent, or a mixture of such polysilazanes. For example, it may be one or more polysilazanes prepared by reacting methyldichlorosilane with ammonia, treating the ammonolysis product with potassium hydride, and quenching the resultant product with methyl iodide or dimethylchlorosilane.

The boroxine reactant is generally a compound corresponding to the formula:

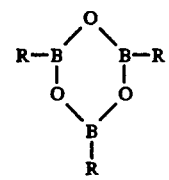

wherein R is an alkoxy, aryloxy, or arylalkoxy group, preferably an alkoxy, phenoxy, alkylphenoxy, phenalkoxy, or alkylphenalkoxy group in whioh any alkyl or alkoxv group contains 1-6 carbons, such as the trimethoxy-, triethoxy-, tripropoxy-, tributoxy-, tripentoxy-, trihexoxy-, triphenoxy-, tritolyloxy-, tri(2-ethylphenoxy)-, tribenzyloxy-, triphenetnoxy-, tri(3-phenylpropoxy)-, tri(4-phenylbutoxy)-, tri(5-phenylpentoxy)-, and tri(6-phenylhexoxy)boroxines, the corresponding triphenalkoxyboroxines having non-linear alkyl chains, tritolylethoxyboroxine, etc. It is preferably trimethoxyboroxine or triphenoxyboroxine. Regardless of the particular boroxine used, the amount employed is about 0.25-20 parts per part by weight of the polysilazane. However, when the boroxine is a trialkoxyboroxine, it is generally preferred to use about 1-6, most preferably about 3-4 parts per part by weight of polysilazane; and, when the boroxine is a triaryloxyboroxine, it is generally preferred to employ about 1-10, most preferably about 6-8 parts per part by weight of polysilazane.

To prepare the organoborosilazane polymers, the neat boroxine reactant (if sufficiently low melting) or a solution thereof in an organic solvent is added to a solution of the polysilazane in an organic solvent to initiate an exothermic reaction which results in the formation of a solution of an organoborosilazane polymer. In a preferred embodiment of the invention in which the process is conducted so as to form a product solution that is directly utilizable as a coating composition, the polysilazane solution that is used is a clear solution; and the total amount of solvent employed is such as to provide a solids content of about 5-75%, preferably about 30-60% by weight.

The solvent employed for the boroxine and/or polysilazane may be any suitable organic solvent, such as hexane, heptane, and other aliphatic hydrocarbons; benzene, toluene, xylene, and other aromatic hydrocarbons; cyclohexanone, 1-methyl-2-pyrrolidone, and other ketones; etc.; and mixtures thereof. When it is desired to use a mixture of solvents for the reaction, the desired mixture may be introduced as the solvent for the polysilazane or for both the polysilazane and the boroxine, or different solvents may be used for the polysilazane and the boroxine.

The boride that is mixed with the organoborosilazane polymer may be a boride of any metal, such as barium, calcium, cobalt, iron, magnesium, manganese, nickel, rhenium, strontium, etc.; but it is preferably a metal of Groups IIIa-VIa of the periodic table or a metal of the lanthanide series. The borides of the actinide series are utilizable but unattractive because of their radioactivity. Exemplary of the preferred borides are the monoborides of titanium, zirconium, hafnium, vanadium, niobium, tantalum, chromium, and tungsten; the diborides of scandium, yttrium, titanium, zirconium, hafnium, vanadium, niobium, tantalum, chromium, and molybdenum; the tetraborides of yttrium, lanthanum, cerium, samarium, and gadolinium; the hexaborides of scandium, yttrium, lanthanum, cerium, neodymium, samarium, and gadolinium; the dodecabromides of yttrium and zirconium, etc.

It is preferred that the boride have an average particle size of about 1-2 micrometers to facilitate the formation of a homogeneous dispersion. Finer and coarser particles are also utilizable, but the dispersions formed from them are less homogeneous when the average particle size is much larger than about 1-2 micrometers, e.g., when it is about 10-20 micrometers. The amount of metal boride employed is about 0.4-1 part per part by weight of the organoborosilazane polymer.

To prepare the dispersions of the invention, the boride is added to a solution of the organoborosilazane polymer in an organic solvent; and the mixture is agitated, e.g., by shaking or ultrasonicating it, to form a homogeneous dispersion. In a preferred embodiment of the invention in which the process is conducted so as to form a dispersion that is directly utilizable as a coating composition, the organoborosilazane polymer solution that is used is a clear solution; and the total amount of solvent employed is such as to provide about 5-75%, preferably about 30-60% by weight of dissolved and dispersed solids in the dispersion.

The organoborosilazane polymer dispersions of the invention are preceramic materials which are useful for making ceramics such as coatings, structural composites, etc; and, like other preceramic materials, they may be used in combination with other ingredients, such as ceramic powders or whiskers, etc., when appropriate.

An application in which they find particular utility is as coating compositions for normally oxidizable materials, especially those which need protection from oxidative deterioration at elevated temperatures. (Such materials include, e.g., fibers tows, hanks, mats, and composites of carbon; carbon or graphite slabs, rods, and structures; and oxidizable metals, such as magnesium, aluminum, silicon, niobium, molybdenum, lanthanum, hafnium, tantalum, tungsten, titanium, and the metals of the lanthanide and actinide series.) When used in such an application in which the substrate is porous, the compositions also serve as infiltrants.

In addition to providing protection from oxidative deterioration, the coating compositions can also serve to improve the physical properties and thermal stability of substrates such as those mentioned above, silica foams, ceramic cloths (e.g., cloths formed from alumina, silica, and/or lithia), etc.

The coating compositions are also useful for patching ceramic coatings formed from the same or different formulations.

When the dispersions are to be used to provide protective ceramic coatings on substrates, the surfaces to be coated are usually cleaned prior to the application of the coating composition in order to improve the bonding of the ceramic coating to the substrate. The bonding can sometimes be further improved by pre-etching the surfaces to be coated.

The coating compositions may be applied to the substrates in any suitable manner, such as by spraying, swabbing, or brushing, to form coatings having the desired thickness, generally a thickness of up to about 1,000 micrometers, frequently a thickness of about 10-250 micrometers. A coating of a desired thickness can be achieved by applying a single coating of that thickness or by applying the precursor polymer coating composition in multiple thinner layers, e.g., by applying the coating composition in layers of about 25-100 micrometers, each layer being dried by driving off the solvent before the next layer is applied.

When temperatures as high as about 200°-250° C. are used to drive off high boiling solvents, some pyrolysis of the preceramic polymer is initiated during the drying of the coating composition. However, higher temperatures, i.e., about 675°-900° C., preferably about 825°-875° C., are required to convert the preceramic coating to a ceramic coating. This pyrolysis may be delayed until the final desired thickness of preceramic coating has been deposited. However, it is generally preferred to pyrolyze each one or two layers of dried preceramic coating before applying the next layer of coating composition. The time required for the pyrolysis is generally about 1-60 minutes, depending on the particular pyrolysis temperature selected. In the preferred embodiment of the invention where the coating is applied in multiple layers, each one or two of which is pyrolyzed before the application of the next layer, and the pyrolysis temperature is about 825°-875° C., it is generally preferred to pyrolyze the first coat for only about five minutes and then to pyrolyze subsequent coats for longer times up to about 15 minutes.

When the coating is intended to protect a substrate from oxidative deterioration at very high temperatures, e.g., temperatures higher than 800° C., each pyrolysis is followed by thermal treatment of the coated substrate at about 1075°-1250° C., preferably about 1100°-1175° C., most preferably about 1125° C., in an atmosphere containing not more than a minor amount of oxygen, e.g., in a nitrogen, argon, or helium atmosphere, to convert the ceramic coating into a homogeneous film. This treatment may be accomplished by raising the temperature in the vessel used for the pyrolysis or by transferring the coated substrate to a vessel maintained at the higher temperature; and it is preferably continued for about five minutes for the first coat and longer periods, e.g., about 15-20 minutes, for subsequent coats.

After each pyrolysis or pyrolysis/heat treatment step employed in providing a ceramic coating, the coated substrate is cooled. Optimum results are attained when this cooling is accomplished at a rate not greater than about 50° C./minute, preferably about 20°-30° C./minute, until the substrate temperature is below 500° C., at which time further cooling may be accomplished at ambient air temperature.

Although not essential, it is preferred to keep the starting polysilazane and the organoborosilazane polymers and compositions formed from it in a dry atmosphere until a layer of ceramic has been formed because of the susceptibility of the preceramic materials to attack by water and other compounds having active hydrogens.

As already indicated, the organoborosilazane polymer dispersions of the invention are useful in preparing a variety of ceramic objects, but the major advantage of the invention is its provision of compositions capable of protecting normally oxidizable materials from oxidative deterioration at elevated temperatures. This advantage is of particular importance in the protection of carbon/carbon composites, graphite, and metals used in aerospace applications, such as engine components, advanced nozzle system components, and high-temperature vehicle structures.

The following examples are given to illustrate the invention and are not intended as a limitation thereof.

EXAMPLE I

Synthesis of Polysilazane

Part A

A suitable reaction vessel was charged with 14L of anhydrous tetrahydrofuran and cooled to about 0° C., after which 1,545 g (13.43 mols) of methyldichlorosilane was added to the vessel, and stirring at about 60 rpm was begun. A slow steady stream of 1,058 g (62.12 mols) of anhydrous ammonia gas was introduced into the vessel at a flow rate such that the reaction pressure was maintained at or below 400 kPa, and the reaction temperature stayed in the range of 0°-10° C. Then the reaction mixture was stirred at 0° C. for about three hours, after which the coolant flow on the vessel was shut off, and the system was put under gentle nitrogen purge to allow the reaction mass to warm to room temperature and the majority of the excess ammonia to vent off. Then the reaction vessel was pressurized with sufficient nitrogen gas to pump the product mass through a bag filter assembly into a holding tank, where it was verified that the filtrate solution was free of particulates.

Part B

The clear filtrate from Part A was discharged into a polymerization vessel and chilled to about 0° C., and a suspension of 3.6 g (0.089 mol) of potassium hydride powder in about 100 mL of anhydrous tetrahydrofuran was added to begin the polymerization reaction. The reaction mixture was maintained at 0° C. for about 8 hours and then allowed to warm gradually to about 22° C. After a total of about 26 hours of polymerization at 0°-22° C., the reaction was quenched by adding about 12.6 g (0.13 mol) of dimethylchlorosilane to the polymerization solution.

The polymer product was isolated by (1) concentrating the product solution to about 4L of volume by vacuum distillation, (2) centrifuging the concentrated solution to obtain a clear supernatant solution and a white precipitate, (3) decanting off the supernatant solution from the precipitate, and (4) flashing off the volatiles from the supernatant solution by vacuum distillation to provide a white solid. Proton NMR spectra of the polymer in deuterated chloroform solvent had resonances consistent with those reported in Seyferth et al.-II for polysilazane and with the presence of a small amount, i.e., 2.4% by weight, of residual tetrahydrofuran.

EXAMPLE II

Synthesis of Organoborosilazane Polymers

A clear solution of 4.0 g of trimethoxyboroxine in a mixture of 1.5 g of xylene and 0.5 g of 1-methyl-2-pyrrolidone was slowly added to a clear solution of 1.0 g of the polysilazane of Example I in a mixture of 1.5 g of xylene and 0.5 g of 1-methyl -2-pyrrolidone. An exothermic reaction occurred to form a solution of an organoborosilazane polymer.

EXAMPLE III

Preparation of Dispersions

Each of several dispersions was prepared by adding 4.8 g of a metal boride to the organoborosilazane polymer solution of Example II and agitating the mixture until a homogeneous dispersion was obtained. The metal borides employed are shown below.

| Dispersion | Metal Boride |
| --- | --- |
| A | $HfB_2$ |
| B | $ZrB_2$ |
| C | $TiB_2$ |
| D | $EuB_6$ |
| E | $SmB_6$ |
| F | $YB_6$ |
| G | $LaB_6$ |
| H | $Cr_3B_4$ |
| I | $NbB_2$ |

EXAMPLE IV

Graphite coupons having nominal dimensions of about 3.8 cm×2.5 cm×0.3 cm were abraded to provided a smooth finish, cleaned, vacuum dried, thoroughly swab-coated in an inert atmosphere with Dispersion A, dried, heated at 100° C. for five minutes, heated to 150° C. at a rate of about 10° C./minute, held at 150° C. for 15-30 minutes, allowed to cool to room temperature, recoated until the coated coupon remained stable at 150° C. for 30 minutes, heated to about 175°-186° C., maintained at that temperature for at least 15 minutes, and cooled to provide coupons having a coating thickness of about 0.08-0.1 mm.

The coatings were then pyrolyzed to ceramic coats by heating the coated coupons to 165° C. at a rate of 5° C./minute, holding at 165° C. for 15 minutes, heating to 285° C. at a rate of 5° C./minute, holding at 285° C. for 30 minutes, heating to 850° C. at a rate of 100° C./minute, holding at 850° C. for 15 minutes, heating to 1250° C., holding at 1250° C. for 15 minutes, and cooling to room temperature.

The effectiveness of the ceramic coats thus obtained in protecting the graphite substrate from oxidation was determined by an oxidation test. The coated specimen was mounted horizontally in a half section of a silicon carbide tube which was used as a holder and which allowed over 99% of the coupon surface to be directly exposed to hot ambient convecting air. The holder and specimen were placed in a box furnace which had been preheated to 1100° C., held there for four hours, removed from the furnace, and quenched in ambient air, after which the cooled specimen was weighed. The oxidation weight loss after four hours was only 1.8%. This compares with a weight loss of 63-70% when uncoated graphite coupons were subjected to the same oxidation test and a weight loss of 52-60% when the example was repeated except that Dispersion A was replaced with the organoborosilazane polymer of Example II.

EXAMPLE V

Example IV was repeated several times except that Dispersion A was replaced with each of the other dispersions of Example III. The oxidation weight losses found when the other dispersions were used are shown below.

| Dispersion | Metal Boride | Oxidation Weight Loss |
| --- | --- | --- |
| B | $ZrB_2$ | 1.2% |
| C | $TiB_2$ | 3.9% |
| D | $EuB_6$ | 0.2% |
| E | $SmB_6$ | 0.6% |
| F | $YB_6$ | 1.6% |
| G | $LaB_6$ | 7.8% |
| H | $Cr_3B_4$ | 18.8% |
| I | $NbB_2$ | 1.7% |

It is obvious that many variations can be made in the products and processes set forth above without departing from the spirit and scope of this invention.

What is claimed is:

1. An intimate dispersion consisting essentially of a metal boride other than silicon boride or aluminum boride in an organic solvent solution containing an organoborosilazane polymer, wherein the amount of metal boride is about 0.4–1 part by weight per one part by weight of the organoborosilazane polymer, said polymer having been prepared by mixing about 0.25–20 parts by weight of a trialkoxy-, triaryloxy-, or tri(arylalkoxy)boroxine with an organic solvent solution of one part by weight of a polysilazane.

2. The dispersion of claim 1 wherein the metal boride is a boride of a Group IIIa-VIa metal.

3. The dispersion of claim 1 wherein the metal boride is a boride of a metal of the lanthanide series.

4. The dispersion of claim 1 wherein the boroxine is a compound corresponding to the formula:

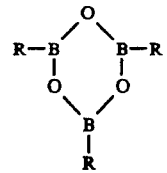

in which R is an alkoxy, phenoxy, alkylphenoxy, phenalkoxy, or alkylphenalkoxy substituent in which any alkyl or alkoxy group contains 1–6 carbons.

5. The dispersion of claim 4 wherein the boroxine is trimethoxyboroxine.

6. The dispersion of claim 1 wherein the polysilazane is a polymer prepared by reacting an organodihalosilane with ammonia, treating the ammonolysis product with a basic catalyst which is capable of deprotonating an NH group that is adjacent to an SiH group, and quenching the resultant product with an electrophilic quenching reagent.

7. The dispersion of claim 6 wherein the organodihalosilane is methyldichlorosilane and the basic catalyst is potassium hydride.

8. The dispersion of claim 1 wherein the metal boride has an average particle size of about 1–2 micrometers.

* * * * *